United States Patent [19]

Barreau et al.

[11] Patent Number: 5,676,831
[45] Date of Patent: Oct. 14, 1997

[54] ISOINDOLINONE DERIVATIVE, PREPARATION THEREOF AND PHARMACEUTICAL COMPOSITIONS CONTAINING SAME

[75] Inventors: Michel Barreau, Montgeron; Michel Cheve, Soisy Sur Seine; Marie-Christine Dubroeucq, Enghein les Bains; Gilles Dutruc-Rosset, Paris; Franco Manfre, Limeil-Brevannes, all of France

[73] Assignee: Rhone-Poulec Rorer S.A., Antony Cedex, France

[21] Appl. No.: 712,282

[22] Filed: Sep. 11, 1996

Related U.S. Application Data

[62] Division of Ser. No. 476,749, Jun. 7, 1995, Pat. No. 5,599,936, which is a division of Ser. No. 286,294, Aug. 5, 1994, Pat. No. 5,494,915, and a division of PCT/FR93/00113, Feb. 4, 1993.

Foreign Application Priority Data

Feb. 7, 1992 [FR] France .................. 92 01382

[51] Int. Cl.$^6$ .................................................. B01D 15/08
[52] U.S. Cl. .................. 210/198.2; 210/502.1; 210/635; 210/656
[58] Field of Search ............ 210/635, 656, 210/198.2, 502.1; 435/280; 502/401, 402, 404, 439

[56] References Cited

U.S. PATENT DOCUMENTS

| | | |
|---|---|---|
| 4,512,898 | 4/1985 | Oi ............................. 210/656 |
| 4,604,207 | 8/1986 | Oi ............................. 210/635 |
| 4,963,254 | 10/1990 | Oi ............................. 210/198.2 |
| 5,051,176 | 9/1991 | Miyano ...................... 210/198.2 |
| 5,080,795 | 1/1992 | Pirkle ........................ 210/643 |
| 5,089,642 | 2/1992 | Hasegawa .................... 556/1 |
| 5,149,426 | 9/1992 | Watabe ....................... 210/198.2 |
| 5,312,924 | 5/1994 | Grell .......................... 546/234 |
| 5,338,529 | 8/1994 | Pirkle ........................ 423/461 |
| 5,387,338 | 2/1995 | Pirkle ........................ 210/198.2 |
| 5,422,004 | 6/1995 | Pirkle ........................ 210/198.2 |
| 5,484,530 | 1/1996 | Pirkle ........................ 210/635 |
| 5,487,831 | 1/1996 | Pirkle ........................ 210/198.2 |
| 5,578,212 | 11/1996 | Pirkle ....................... 210/656 |

OTHER PUBLICATIONS

Okamoto, J. Am. Chem. Soc. 106, 1984, pp. 5357–5359.

*Primary Examiner*—Ernest G. Therkorn
*Attorney, Agent, or Firm*—Raymond S. Parker, III; Martin F. Savitzky

[57] ABSTRACT

The present invention relates to a new isoindolinone derivative of formula:

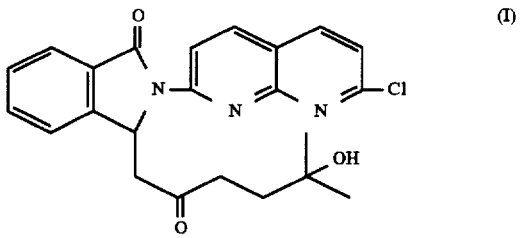

in racemic form or in the form of its enantiomers, as well as its salts, its preparation and the pharmaceutical compositions which contain it.

4 Claims, No Drawings

ISOINDOLINONE DERIVATIVE, PREPARATION THEREOF AND PHARMACEUTICAL COMPOSITIONS CONTAINING SAME

This is a divisional of application Ser. No. 08/476,749 filed on Jun. 7, 1995, now U.S. Pat. No. 5,599,936, which, in turn is a division of Ser. No. 08/286,294, filed on Aug. 5, 1994, now U.S. Pat. No. 5,494,915, and a division of International Application PCT/FR93/00113, filed Feb. 4, 1993 and which designated the U.S., now abandoned.

The present invention relates to a new isoindolinone derivative of formula:

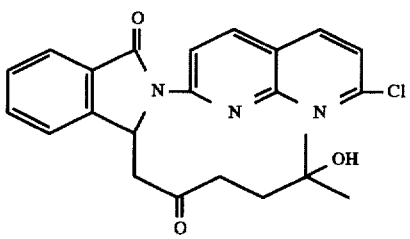

(I)

in racemic form or in the form of its enantiomers, as well as its salts, its preparation and the pharmaceutical compositions which contain it.

The product of formula (I) has noteworthy anxiolytic, hypnotic, anticonvulsive, antiepileptic and muscle-relaxant properties.

European Patent EP 0,274,930 has described isoindolinone derivatives of general formula:

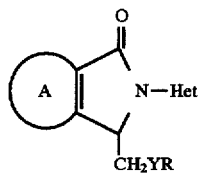

(II)

in which, more particularly, A forms an isoindoline nucleus with the pyrrole ring, Het represents a naphthyridinyl radical which is substituted with a halogen atom, Y represents a radical CO and R represents a substituted or unsubstituted alkyl radical containing 1 to 10 carbon atoms, which derivatives have noteworthy therapeutic properties.

Among these products, that for which A forms an isoindoline nucleus with the pyrrole ring, Het represents a 2-(7-chloro-1,8-naphthyridinyl) radical, Y represents a radical CO and R represents a 3-methyl-butyl radical, in racemic form or in the form of its enantiomers, in particular the dextrorotatory isomer, exhibits a particularly powerful activity associated with low toxicity. On the other hand, the products of general formula (II) for which R represents an alkyl radical which is substituted with a primary hydroxyl radical, such as a 3-hydroxypropyl radical, exhibit the same type of activity to a markedly lower degree and they are consequently difficult to exploit in the pharmaceutical industry.

It has now been found, and this forms the subject of the present invention, that the products of general formula (II), in which R represents an alkyl radical which is substituted with a tertiary hydroxyl radical, and in particular the product of formula (I) in racemic form or in the form of its enantiomers, surprisingly and unexpectedly exhibits an activity which is at least as interesting as that of the corresponding product for which R represents a 3-methylbutyl radical.

According to the present invention, the product of formula (I), in racemic form, may be obtained by hydration of the product of formula:

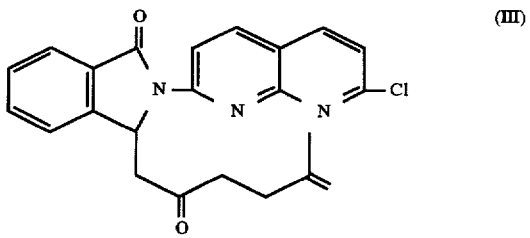

(III)

in racemic form, by working in the presence of an acid in an aqueous-organic medium.

An ether such as tetrahydrofuran or dioxane is preferably used as organic solvent.

An inorganic acid such as sulphuric acid is preferably used as acid.

The hydration is generally carried out at a temperature between 0° C. and 50° C. and preferably at about 20° C.

The enantiomers of the product of formula (I) may be obtained:

either by separation on a chiral phase which is suitable for the enantiomers constituting the racemic product of formula (I), or by separation on a chiral phase which is suitable for the enantiomers constituting the racemic product of formula (III), followed by hydration of each of the enantiomers obtained.

The separation of the enantiomers constituting the racemic product of formula (I) is generally carried out by high performance liquid chromatography on a column of silica coated with cellulose trisphenylcarbamate while eluting with a suitable solvent such as an ethanol/hexane mixture. A phase prepared under the conditions described in J. Amer. Chem. Soc., 106, 5357 (1984) is preferably used.

The separation of the enantiomers constituting the racemic product of formula (III) is generally carried out by high performance liquid chromatography on a phase of modified Pirkle type while eluting with a suitable solvent such as a hexane/methylene chloride mixture.

A phase for which the chiral selector, which is preferably 3,5-dinitro-L-benzoylleucine, is spaced form the silica by an aminoalkanoyl arm containing 3 to 14 carbon atoms and which is attached to the amine functions of an aminopropyl silica and in which the free silanol functions are blocked by trialkylsilyl radicals, is preferably used as chiral phase.

This chiral phase, which constitutes another subject of the present invention, may be defined by the following structure:

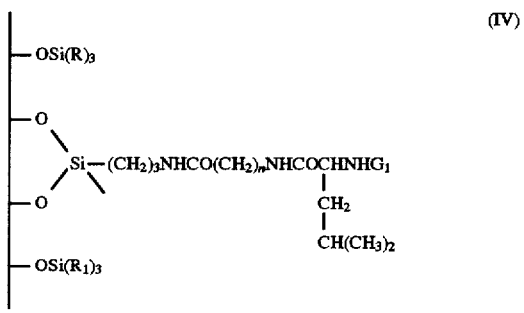

(IV)

in which the symbols R, which may be identical or different, and $R_1$, which may be identical or different, represent alkyl radicals containing 1 to 10 carbon atoms, $G_1$ represents an electron-withdrawing group and n represents an integer between 3 and 13 inclusively.

Preferably, one of the symbols R represents an alkyl radical containing 7 to 10 carbon atoms and the other two represent an alkyl radical containing 1 or 2 carbon atoms and preferably a methyl radical, the symbols $R_1$ are identical and represent a methyl or ethyl radical, $G_1$ represents a benzoyl radical which is optionally substituted, preferably with one or more nitro radicals such as the 3,5-dinitrobenzoyl radical, and n is equal to 10.

The new chiral phase according to the invention may be prepared by the action on an aminopropyl silica of an aminoalkanoic acid anhydride containing 3 to 14 carbon atoms in which the amine function is protected by a protecting group such as the tert-butoxycarbonyl radical, followed by blocking some of the silanol functions by —Si(R)$_3$ radicals as defined above, then, after removal of the protecting group for the amine function, amidation using L-leucine in which the amine function is protected by an electron-withdrawing group $G_1$ as defined above, and finally by blocking the residual silanol functions by —Si(R$_1$)$_3$ radicals as defined above.

The action of a protected aminoalkanoic acid anhydride on the aminopropyl silica is generally carried out by working in an anhydrous organic solvent such as dimethylformamide, at a temperature of about 20° C.

The blocking of the silanol functions by —Si(R3) groups as defined above is carried out by the action of a halotrialkylsilane on the aminopropyl silica to which aminoalkanoyl residues have been grafted, working in an organic solvent such as methylene chloride in the presence of a basic agent such as pyridine.

Removal of the protecting groups for the aminoalkanoyl residues is generally carried out, when the protecting group is a tert-butoxycarbonyl radical, by the action of trifluoroacetic acid in an organic solvent such as methylene chloride.

The amidation using L-leucine in which the amine function is protected is carried out in the presence of a condensing agent such as N-ethoxy-carbonyl-2-ethoxy-1,2-dihydroquinoline, working in an anhydrous organic solvent such as dimethylformamide.

The blocking of the residual silanol functions by —Si(R$_1$)$_3$ radicals as defined above is generally carried out using trialkylsilylimidazole, working in an organic solvent such as methylene chloride.

The hydration of each of the enantiomers obtained is carried out under the conditions described above for the hydration of the corresponding racemic product.

The product of formula (III) may be obtained by dealkoxycarbonylation of a product of general formula:

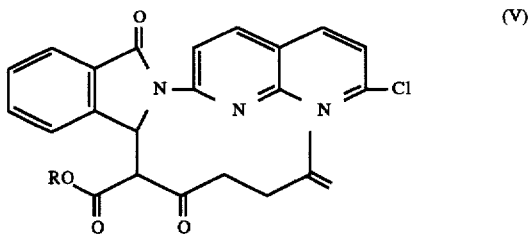

(V)

in which R represents a straight or branched alkyl radical containing 1 to 4 carbon atoms, by the action of lithium chloride in an organic solvent such as dimethyl sulphoxide at a temperature between 0° and 50° C.

The product of general formula (V) may be obtained by the action of an ester of general formula:

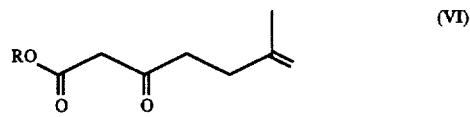

(VI)

in which R is defined as above on 3-chloro-2-(7-chloro-1, 8-naphthyridin-2-yl)-1-isoindolinone, by working in the presence of a strong inorganic base such as sodium hydride in an anhydrous organic solvent such as dimethylformamide.

The ester of general formula (VI) may be obtained under the conditions described by V. B. Rao et al., J. Amer. Chem. Soc., 107, 5732 (1985).

3-Chloro-2-(7-chloro-1,8-naphthyridin-2-yl)-1-isoindolinone may be prepared under the conditions described in European Patent EP 0,274,930.

The product of formula (I), in racemic form and its enantiomers, in particular the dextrorotatory enantiomer, optionally in the form of salts, exhibit particularly advantageous pharmacological properties which make them useful as anxiolytic, hypnotic, anticonvulsive, antiepileptic and muscle-relaxant agents. In particular, they have a good in vitro affinity for benzodiazepine receptor sites at concentrations with values between 0.5 and 1 nM according to the technique described by J. C. Blanchard and L. Julou, J. Neurochemistry, 40, 601 (1983) based on the work of Squires and Braestrup, Nature, 266, 732 (1977).

They have shown themselves to be active in mice at doses generally between 0.05 and 0.5 mg/kg via the oral route with respect to convulsions, induced by pentetrazol according to a similar technique to that of Everett and Richards, J. Pharmacol., 81, 402 (1944).

The new product of formula (I) and its salts are of low toxicity. Their LD$_{50}$ is greater than 300 mg/kg via the oral route in mice.

For medicinal use, the new product of formula (I) may be used as it is or in the state of a pharmaceutically acceptable salt, that is to say which is non-toxic at the doses used.

Pharmaceutically acceptable salts which may be mentioned are the addition salts with inorganic acids such as hydrochlorides, sulphates, nitrates and phosphates or organic acids such as acetates, propionates, succinates, benzoates, fumarates, maleates, methanesulphonates, isethionates, theophyllineacetates, salicylates, phenolphthaleinates or methylenebis-α-oxynaphthoates or substitution derivatives of these compounds.

The examples which follow illustrate the present invention.

EXAMPLE 1

To a suspension of 2 g of (R,S)-2-(7-chloro-1,8-naphthyridin-2-yl)-3-(5-methyl-2-oxo-5-hexen-1-yl)-1-isoindolinone in 20 cm$^3$ of 1,4-dioxane are added, at a temperature of about 20° C., 20 cm$^3$ of aqueous 35% sulphuric acid solution (w/v). The yellow solution is stirred for 12 hours, followed by the addition of 20 g of crushed ice. The pH of the reaction mixture is brought to about 7 by addition of aqueous 1N sodium hydroxide solution. It is then extracted with 3 times 100 cm$^3$ of ethyl acetate. The combined organic phases are washed twice with 50 cm$^3$ of water, dried over magnesium sulphate and concentrated to dryness under reduced pressure at a temperature of about 40° C. The residue is recrystallized in acetonitrile to yield 1.2 g of (R,S)-2-(7-chloro-1,8-naphthyridin-2-yl)-3-(5-methyl-5-hydroxy-2-oxohexyl)-1-isoindolinone, melting at 140° C.

(R,S)-2-(7-Chloro-1,8-naphthyridin-2-yl)-3-(5-methyl-2-oxo-5-hexen-1-yl)-1-isoindolinone may be prepared in the following way:

To a solution of 9.3 g of ethyl 2-[2-(7-chloro-1,8-naphthyridin-2-yl)-3-oxo-1-isoindolinyl]-6-methyl-3-oxo-6-heptenoate (mixture of A and B forms) in 60 cm$^3$ of dimethyl sulphoxide are added, at a temperature of about 25° C., 11.5 g of lithium chloride and 4.6 cm$^3$ of water. The reaction mixture is heated to reflux for 20 minutes, cooled to a temperature of about 30° C., diluted with 60 cm$^3$ of water and then cooled to a temperature of about 5° C. A solid which precipitates is separated by filtration, washed successively twice with 25 cm$^3$ of water, once with 20 cm$^3$ of ethanol and twice with 25 cm$^3$ of diisopropyl ether. After air-drying, 7.2 g of (R,S)-2-(7-chloro-1,8-naphthyridin-2-yl)-3-(5-methyl-2-oxo-5-hexen-1-yl)-1-isoindolinone are thus obtained, melting at 184° C.

Ethyl 2-[2-(7-chloro-1,8-naphthyridin-2-yl)-3-oxo-1-isoindolinyl]-6-methyl-3-oxo-6-heptenoate (mixture of A and B forms) may be prepared in the following way:

1.7 g of an oily suspension (50% by weight) of sodium hydride are added to 100 cm$^3$ of anhydrous dimethylformamide, under an argon atmosphere, at a temperature of about 10° C. 9.8 g of ethyl 6-methyl-3-oxo-6-heptenoate in 25 cm$^3$ of anhydrous dimethylformamide are subsequently added. The suspension is stirred for 30 minutes and the temperature is allowed to return to about 20° C., followed by the addition of 11.6 g of 3-chloro-2-(7-chloro-1,8-naphthyridin-2-yl)-1-isoindolinone. The reaction mixture is stirred for 4 hours at a temperature of about 20° C. and is then poured into 250 cm$^3$ of water. The aqueous phase, which is acidified by the addition of 25 cm$^3$ of aqueous 1N hydrochloric acid solution, is extracted twice with 200 cm$^3$ of dichloromethane. The organic phases are combined and washed twice with 50 cm$^3$ of water, dried over magnesium sulphate and concentrated to dryness under reduced pressure at 40° C. The oily residue is purified by chromatography on silica [eluent:ethyl acetate/cyclohexane (30/70 by volume)]. The fractions containing the expected product are combined and concentrated to dryness under reduced pressure at 40° C. After crystallization in diisopropyl ether, 9.4 g of ethyl 2-[2-(7-chloro-1,8-naphthyridin-2-yl)-3-oxo-1-isoindolinyl]-6-methyl-3-oxo-6-heptenoate (mixture of A and B forms) are thus obtained, melting at 125° C.

Ethyl 6-methyl-3-oxo-6-heptenoate may be prepared according to the method described by V. B. Rao et al., J. Amer. Chem. Soc., 107, 5732 (1985).

3-Chloro-2-(7-chloro-1,8-naphthyridin-2-yl)-1-isoindolinone may be prepared according to the method described in European Patent EP 0.274,930.

EXAMPLE 2

Starting from 0.86 g of (R,S)-2-(7-chloro-1,8-naphthyridin-2-yl)-3-(5-methyl-5-hydroxy-2-oxohexyl)-1-isoindolinone, the following are successively eluted on separation by high performance liquid chromatography on 350 g of support consisting of silica coated with cellulose trisphenylcarbamate prepared according to J. Amer. Chem. Soc., 106, 5357 (1984) and contained in a column of length 19 cm and diameter 6 cm with the mixture ethanol/hexane (1/1 by volume) as mobile phase at a flow rate of 30 cm$^3$/minute:

0.38 g of (−)-2-(7-chloro-1,8-naphthyridin-2-yl)-3-(5-methyl-5-hydroxy-2-oxohexyl)-1-isoindolinone melting at 178° C., the optical rotation of which is $[a]^{20}_D=$ −105°±2° (c=0.75; chloroform), followed by 0.41 g of (+)-2-(7-chloro-1,8-naphthyridin-2-yl)-3-(5-methyl-5-hydroxy-2-oxohexyl)-1-isoindolinone melting at 178° C., the optical rotation of which is $[a]^{20}_D=$ +104°±2° (c=0.81; chloroform).

EXAMPLE 3

By working as in Example 1, but using 40 g of (+)-2-(7-chloro-1,8-naphthyridin-2-yl)-3-(5-methyl-2-oxo-5-hexen-1-yl)-1-isoindolinone, 8 mg of (+)-2-(7-chloro-1,8-naphthyridin-2-yl)-3-(5-methyl-5-hydroxy-2-oxohexyl)-1-isoindolinone are obtained, the characteristics of which are identical to those of the product obtained in Example 2.

(+)-2-(7-Chloro-1,8-naphthyridin-2-yl)-3-(5-methyl-2-oxo-5-hexen-1-yl)-1-isoindolinone may be obtained in the following way:

Starting from 2.8 g of (R,S)-2-(7-chloro-1,8-naphthyridin-2-yl)-3-(5-methyl-2-oxo-5-hexen-1-yl)-1-isoindolinone, the following are successively eluted on separation by high performance liquid chromatography on 400 g of support, the preparation of which is described below, contained in a column of length 26 cm and diameter 6 cm with the mixture hexane/methylene chloride (100/15 by volume) as mobile phase at a flow rate of 60 cm$^3$/minute:

0.76 g of (+)-2-(7-chloro-1,8-naphthyridin-2-yl)-3-(5-methyl-2-oxo-5-hexen-1-yl)-1-isoindolinone melting at 178° C., after recrystallization in ethanol and for which the optical rotation is $[a]^{20}_D=$+141°±3° (c=0.53; chloroform)

0.45 g of (−)-2-(7-chloro-1,8-naphthyridin-2-yl)-3-(5-methyl-2-oxo-5-hexen-1-yl)-1-isoindolinone melting at 178° C., after recrystallization in ethanol and for which the optical rotation is $[a]^{20}_D=$−136°±3° (c=0.43; chloroform).

The support may be prepared in the following way:

Aminopropyl silica (253 g; 100 Å-10 μm-NH$_2$; Macherey-Nagel) are suspended in 850 cm$^3$ of dimethylformamide which has been dried over 4 Å molecular sieves, in a 2-liter three-necked round-bottomed flask. 11-N-(tert-butoxycarbonyl)aminoundecanoic acid anhydride (40 g) are added. The reaction mixture is stirred for 16 hours at 20° C. and is then filtered on a sinter funnel. The silica is washed successively with 150 cm$^3$ of dimethylformamide, twice 200 cm$^3$ of tetrahydrofuran and twice 200 cm$^3$ of methylene chloride. The silica thus washed is resuspended in 850 cm$^3$ of dimethylformamide. 40 g of 11-N-(tert-butoxycarbonyl) aminoundecanoic acid anhydride are added and the mixture is then stirred for 6 hours at 20° C. The silica is filtered on a sinter funnel and washed successively with 150 cm$^3$ of dimethylformamide, twice 200 cm$^3$ of methylene chloride, 200 cm$^3$ of methanol and 150 cm$^3$ of methylene chloride. After drying the silica at 20° C. under reduced pressure (20 mm of mercury; 2.7 kPa), 267 g of silica referred to by the name "BOC—C$_{11}$–C$_3$— (silica)" are obtained in the form of a white powder, the structure of which is confirmed by the infra-red spectrum and the elemental analysis (found) of which is: C %=8.1; H %=1.7; N %=1.4.

266 g of "BOC—C$_{11}$–C$_3$— (silica)", 800 cm$^3$ of methylene chloride and 30 cm$^3$ of pyridine are introduced into a 2-liter three-necked round-bottomed flask. Dimethyloctylchlorosilane (230 cm$^3$) are added dropwise over 10 minutes, followed by stirring overnight. The solid obtained is separated out by filtration and is then washed successively twice with 500 cm$^3$ of methylene chloride, twice with 500 cm$^3$ of methanol, twice with 500 cm$^3$ of methylene chloride and twice with 250 cm$^3$ of ethyl ether. After drying at 20° C. under reduced pressure (20 mm of mercury; 2.7 kPa), 274 g of silica referred to by the name "BOC—$C_{11}$-$C_3$— (silica) -O—Si($CH_3$)$_2$($CH_2$)$_7$$CH_3$" are obtained, the structure of which is confirmed by the infra-red spectrum and the elemental analysis (found) of which is: C %=10.0; H %=2.1; N %=1.3.

274 g of "BOC—$C_{11}$-$C_3$— (silica)-O—Si($CH_3$)$_2$($CH_2$)$_7$$CH_3$" are suspended in 800 cm$_3$ of a 6% by volume solution of trifluoroacetic acid in methylene chloride in a 2-liter three-necked round-bottomed flask. The reaction mixture is stirred for 20 hours at 20° C. The silica is separated by filtration on a sinter funnel, washed twice with 300 cm$^3$ of methylene chloride, twice 500 cm$^3$ of a 30% diisopropylethylamine solution in methylene chloride for 30 minutes, twice 500 cm$^3$ of methanol and with 500 cm$^3$ of ethyl ether. After drying at 20° C. under reduced pressure (20 mm of mercury; 2.7 kPa), 269 g of silica referred to by the name "$C_{11}$-$C_3$— (silica)-O—Si($CH_3$)$_2$($CH_2$)$_7$$CH_3$" are obtained, the elemental analysis (found) of which is: C%=8.4; H%=1.7; N%=1.2.

266 g of "$C_{11}$-$C_3$— (silica)-O—Si($CH_3$)$_2$($CH_2$)$_7$$CH_3$" are suspended in 800 cm$^3$ of dimethylformamide which has been dried over 4 Å molecular sieves in a 2-liter three-necked round-bottomed flask. 27.5 g of 3,5-dinitrobenzoyl-L-leucine and 20 g of 2-N-ethoxycarbonylethoxy-1,2-dihydroquinoline are added. The reaction mixture is stirred for 1 night. The silica is separated by filtration on a sinter funnel and is then washed twice with 500 cm$^3$ of methylene chloride, twice with 500 cm$^3$ of tetrahydrofuran, with 500 cm$^3$ of dimethylformamide and with 500 cm$^3$ of methylene chloride. The silica thus washed is resuspended in 800 cm$^3$ of dimethylformamide. 27.5 g of 3,5-dinitrobenzoyl-L-leucine and 20 g of 2-N-ethoxycarbonylethoxy-1,2-dihydroquinoline are successively added, followed by stirring overnight at 20° C. The silica is separated out by filtration,on a sinter funnel and is washed successively twice with 500 cm$^3$ of methylene chloride, twice with 500 cm$^3$ of tetrahydrofuran, twice with 500 cm$^3$ of methanol and twice with 500 cm$^3$ of ethyl ether. After drying at 60° C. under reduced pressure (20 mm of mercury; 2.7 kPa), 273 g of silica referred to by the name "DBN-L-Leu-$C_{11}$-$C_3$— (silica)-O—Si ($CH_3$)$_2$($CH_2$)$_7$$CH_3$" are obtained, which silica is resuspended in 800 cm$^3$ of methylene chloride. Trimethylsilylimidazole (350 cm$^3$) are added over 15 minutes, followed by stirring for 1 night. The silica is filtrated out by filtration and is washed successively twice with 300 cm$^3$ of tetrahydrofuran, twice with 300 cm$^3$ of methanol, twice with 300 cm$^3$ of acetone and twice with 300 cm$^3$ of methylene chloride. After drying at 60° C. under reduced pressure (20 mm of mercury; 2.7 kPa), 275 g of silica referred to by the name "DBN-L-Leu-$C_{11}$-$C_3$— (silica)-[O—Si($CH_3$)$_2$($CH_2$)$_7$$CH_3$]— [O—Si($CH_3$)$_3$]" are obtained in the form of a pale yellow powder, the structure of which is confirmed by the infra-red spectrum and the elemental analysis (found) of which is: C%=12.8; H%=2.3; N%=2.2.

11-N-(tert-Butoxycarbonyl)aminoundecanoic acid anhydride may be prepared in the following way:

30.1 g of 11-N-(tert-butoxycarbonyl)aminoundecanoic acid are dissolved in 480 cm$^3$ of ethyl acetate. This solution is cooled to 5° C. and, while maintaining this temperature, a solution of dicyclohexylcarbodiimide (10.63 g) in 120 cm$^3$ of ethyl acetate is then added over 10 minutes. The reaction mixture is stirred for 1 hour at 5° C. and then for 16 hours at a temperature of about 20° C. A precipitate forms which is separated by filtration and washed with 30 cm$^3$ of ethyl acetate. The filtrate is concentrated to dryness under reduced pressure (20 mm of mercury; 2.7 kPa) at 30° C. The solid obtained is dried at 20° C. under reduced pressure (20 mm of mercury; 2.7 kPa). 31 g of 11-N-(tert-butoxycarbonyl) aminoundecanoic acid anhydride are thus obtained, with a yield of about 100%.

11-N-(tert-Butoxycarbonyl)aminoundecanoic acid may be prepared in the following way:

11-aminoundecanoic acid (160 g), 2 liter of dioxane, 1.3 liters of distilled water, 208 g of sodium carbonate and 173 g of di-tert-butyl dicarbonate are successively introduced into a 4-liter three-necked round-bottomed flask fitted with a mechanical stirrer and a condenser. The reaction mixture is heated to boiling for 16 hours. A clear solution is thus obtained. After cooling to 20° C., the reaction mixture is poured onto 800 g of ice and then acidified to pH=3–4 by addition of 4N hydrochloric acid. A white precipitate is thus obtained, which is separated out by filtration, washed with 300 cm$^3$ of water and dried at 20° C. under reduced pressure (20 mm of mercury; 2.7 kPa). 11-N-(tert-butoxycarbonyl) aminoundecanoic acid (232 g) are thus obtained, with a yield of 95%, the melting point of which (68° C.) is in agreement with that which is given in J. Org. Chem., 41, 1350 (1976).

The present invention also relates to the medicaments which contain the products of formula (I) in the pure state or in the form of compositions in which they are combined with an adjuvant, a diluent and/or a coating agent which are compatible and pharmaceutically acceptable. These medicaments may be employed orally, rectally, parenterally or percutaneously.

Tablets, pills, powders (generally in gelatin capsules) or granules may be used as solid compositions for oral administration. In these compositions, the active product according to the invention is mixed with one or more inert diluents such as sucrose, lactose or starch. These compositions may also contain substances other than diluents, for example a lubricating agent such as magnesium stearate.

Pharmaceutically acceptable emulsions, solutions, suspensions, syrups and elixirs containing inert diluents such as water or paraffin oil may be used as liquid compositions for oral administration. These compositions may also contain substances other than diluents, for example wetting, sweetening or flavouring agents.

The compositions according to the invention for parenteral administration may be aqueous or non-aqueous sterile solutions, suspensions or emulsions. Propylene glycol, a polyethylene glycol, vegetable oils, in particular olive oil or injectable organic esters, for example ethyl oleate, may be used as solvent or vehicle. These compositions may also contain adjuvants, in particular wetting, emulsifying and dispersing agents. The sterilization may be achieved in several ways, for example using a bacteriological filter, by incorporating sterilizing agents into the composition, by irradiation or by heating. They may also be prepared in the form of sterile solid compositions which may be dissolved at the time of use into sterile water or any other injectable sterile medium.

The compositions for rectal administration are suppositories which may contain, besides the active product, excipients such as cocoa butter or suppocire.

The compositions for percutaneous administration are creams, ointments, lotions and liniments, in which the active product is combined with liquid or pasty excipients, preferably in combination with a vehicle which promotes percutaneous migration.

The medicaments and compositions according to the invention are particularly useful in human therapy for their anxiolytic, hypnotic, anticonvulsive, antiepileptic and muscle-relaxant action.

In human therapy, the doses depend upon the desired effect and the duration of the treatment; they are generally between 10 and 500 mg per day via the oral route for an adult.

Generally speaking, the doctor will determine the dosage which he considers to be the most suitable, depending on the age, the weight and all the other personal factors of the subject to be treated.

The example which follows, given without any limitation being implied, illustrates a composition according to the invention.

EXAMPLE

Tablets containing a 10 mg dose of active product and having the following composition are prepared according to the usual technique:

| | |
|---|---|
| 2-(7-chloro-1,8-naphthyridin-2-yl)-3-(5-methyl-5-hydroxy-2-oxohexyl)-1-isoindolinone | 0.01 g |
| starch | 0.200 g |
| precipitated silica | 0.036 g |
| magnesium stearate | 0.004 g |

What is claimed is:

1. A phase of modified Pirkle type comprising the structure:

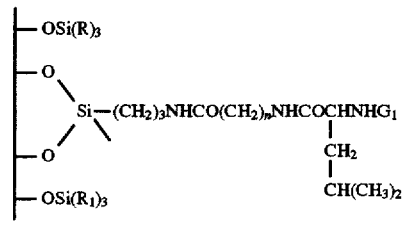

wherein the symbols R, which may be identical or different, and $R_1$, which may be identical or different, represent alkyl radicals containing 1 to 10 carbon atoms, $G_1$ represents an electron-withdrawing group and n represents an integer between 3 and 13 inclusively.

2. The phase of modified Pirkle type according to claim 1 wherein one of the symbols R represents an alkyl radical containing 7 to 10 carbon atoms and the other two represent an alkyl radical containing 1 or 2 carbon atoms the symbols $R_1$ are identical and represent a methyl or ethyl radical, $G_1$ represents a benzoyl radical which is optionally substituted with one or more nitro radicals and n is equal to 10.

3. The phase of modified Pirkle type according to claim 2 wherein $G_1$ represents a 3,5-dinitrobenzoyl radical.

4. The phase of modified Pirkle type according to claim 2 wherein R represents a methyl radical.

* * * * *